(12) United States Patent
Kawate et al.

(10) Patent No.: US 8,982,345 B2
(45) Date of Patent: Mar. 17, 2015

(54) OPTICAL CHARACTERISTIC MEASURING APPARATUS

(75) Inventors: Etsuo Kawate, Ibaraki (JP); Miroslav Hain, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 42 days.

(21) Appl. No.: 14/003,201

(22) PCT Filed: Mar. 8, 2012

(86) PCT No.: PCT/JP2012/055945
§ 371 (c)(1),
(2), (4) Date: Sep. 4, 2013

(87) PCT Pub. No.: WO2012/121323
PCT Pub. Date: Sep. 13, 2012

(65) Prior Publication Data
US 2014/0002825 A1    Jan. 2, 2014

(30) Foreign Application Priority Data
Mar. 8, 2011    (JP) .................. 2011-050104

(51) Int. Cl.
*G01N 21/49*    (2006.01)
*G01N 21/47*    (2006.01)
(Continued)

(52) U.S. Cl.
CPC .......... *G01N 21/4738* (2013.01); *G01N 21/474* (2013.01); *G01N 21/59* (2013.01);
(Continued)

(58) Field of Classification Search
USPC ................ 356/335–343, 445–448, 236, 319; 250/574, 458.1
See application file for complete search history.

(56) References Cited

U.S. PATENT DOCUMENTS 5,127,729 A * 7/1992 Oetliker et al. ............... 356/317
5,210,418 A    5/1993 Harrick et al.
(Continued)

FOREIGN PATENT DOCUMENTS

JP    8-501880 A    2/1996
JP    11-183320 A    7/1999
(Continued)

OTHER PUBLICATIONS

Article entitled "Measurement method of optical scatter using a STAR GEM as a scatterometer" by Etsuo Kawate, 2008, Proc. of SPIE Vol. 7065; pp. 706515-1-706516-9.
(Continued)

*Primary Examiner* — Hoa Pham
(74) *Attorney, Agent, or Firm* — McCormick, Paulding & Huber LLP

(57) ABSTRACT

In an apparatus for measuring an optical characteristic of a sample, one object of the present invention is to provide an apparatus capable of measuring hemispherical total reflectance, hemispherical total transmittance, and light distribution, and to achieve a reduction in measurement time and an improvement in precision of the quantitative analysis of hemispherical total reflectance (transmittance). In a double ellipsoidal optical system which is an optical system in which one focal points of two ellipsoidal mirrors are positioned as a common focal point, and three focal points are aligned in a straight line, the double ellipsoidal optical system is composed of a partial ellipsoidal mirror 2, such as a quarter ellipsoidal mirror, and a belt-shape ellipsoidal mirror 1. By disposing, on a position of a focal point of the partial ellipsoidal mirror, a hemispherical detection optical system having a hemispherical lens or a rotational parabolic mirror, light scattered by an object, reflected by the partial ellipsoidal mirror, and focused on the point is photographed by for example a CCD camera 6 via a hemispherical lens and a taper fiber 5 so as to measure an optical characteristic of the object.

9 Claims, 18 Drawing Sheets

(51) Int. Cl.
*G01N 21/59* (2006.01)
*G02B 19/00* (2006.01)

(52) U.S. Cl.
CPC *G01N2021/4714* (2013.01); *G01N 2201/0637* (2013.01); *G02B 19/0023* (2013.01); *G02B 19/0085* (2013.01)
USPC ............ 356/338; 356/339; 356/236; 356/319

(56) References Cited

U.S. PATENT DOCUMENTS

| | | | |
|---|---|---|---|
| 5,313,542 A | | 5/1994 | Castonguay |
| 5,471,299 A | | 11/1995 | Kaye et al. |
| 5,767,967 A | * | 6/1998 | Yufa ............................. 356/336 |
| 6,128,093 A | | 10/2000 | Niikura |
| 6,636,308 B1 | * | 10/2003 | Tsutsui et al. ................ 356/338 |
| 2002/0041374 A1 | | 4/2002 | Ohshima et al. |
| 2004/0008346 A1 | | 1/2004 | Kawate |
| 2004/0169863 A1 | | 9/2004 | Kawate |

FOREIGN PATENT DOCUMENTS

| | | |
|---|---|---|
| JP | 2000180351 A | 6/2000 |
| JP | 2002188999 A | 7/2002 |
| JP | 2004045065 A | 2/2004 |
| JP | 2004257956 A | 9/2004 |
| JP | 2006234681 A | 9/2006 |
| JP | 2010276363 A | 12/2010 |

OTHER PUBLICATIONS

PCT Search Report for PCT Serial No. PCT/JP2012/055945 dated May 29, 2012.
E Kawate: "Diffuse Reflectance and Transmittance Measurements Using a STAR GEM Optical Accessory", Measurement 2009, Proceedings of the 7th International Conference, 2009, pp. 270-273, XP55126565, Retrieved from the Internet: URL: http://www.measurement.sk/M2009/proceedings/270_Kawatel.pdf.
European Search Report for Serial No. EP12755428 dated Jul. 4, 2014.

* cited by examiner

First Image

Second Image

Third Image

2 : Quarter Ellipsoidal Mirror

1 : Belt-shaped Ellipsoidal Mirror

Fourth Image

7 : RMI Mirror

2 : Quarter Ellipsoidal Mirror

1 : Belt-shaped Ellipsoidal Mirror

Horizontal Axis: Scattering Angle
Vertical Axis: Outputs measured by CCD Camera

OPTICAL CHARACTERISTIC MEASURING APPARATUS

CROSS REFERENCE TO RELATED APPLICATIONS

The present application claims priority from International Patent Application Serial No. PCT/JP2012/055945 filed Mar. 8, 2012 and Japanese Patent Application No. 2011-050104 filed on Mar. 8, 2011, the contents of which are hereby incorporated by reference into this application.

TECHNICAL FIELD

The present invention relates to a highly-sensitive optical characteristic measuring apparatus capable of causing light to fall on an object such as a sample, and measuring light intensity and spatial distribution of scattered light from the sample. In particular, the present invention relates to a scatterometer capable of measuring efficiently total spherical scatter of an object.

BACKGROUND ART

In recent years, improvements in measurement precision of an optical characteristic inspection apparatus has been needed in precise measurement in the manufacture of electronic parts such as a semiconductor product, or in the field of nanotechnologies.

Interactions between material and light falling on and going through the material can be classified into five types: specular reflection, diffuse reflection, (specular) transmission, diffuse transmission, and light absorption. More specifically, reflection and transmission phenomena include specular reflection in which an incident angle and a reflection angle are equal to each other, (specular) transmission in which an incident angle and a transmitted light angle are equal to each other, and scattering in which, for one incident angle, only reflected light for the opaque material, or both reflected light and transmitted light for the transparent material are produced toward a large space (scattering phenomenon which is a combination of diffuse reflection and diffuse transmission).

Conventionally, in order to measure specular reflectance and (specular) transmittance, different accessories are used to measure relative reflectance and absolute transmittance. A drawback of this method lies in the fact that their measurement precisions of measured quantities differs from each other. In order to overcome the drawback, the present inventor has developed an apparatus in which transmittance measurement and reflectance measurement are integrated (see Japanese Patent Application Laid-Open Publication No. 2004-257956; Japanese Patent Application Laid-Open Publication No. 2004-45065; and Japanese Patent Application Laid-Open Publication No. 2006-234681).

Light scattering phenomena due to material include complete scattering of light scattered uniformly in a whole space ($4\pi$ space) and partial scattering of light scattered in a certain partial space. A loosely-packed fine powder is one example of the former complete scattering, while there are numerous examples of the latter around us. More specifically, a ceramic tile, a painted surface, fabric (warp and weft), and a paper surface (paper fiber has a net-like structure) are examples of the latter. The specular reflection and (specular) transmission phenomena can be considered as a limit of "a certain partial space" in this partial scattering. As will be seen from the above examples, in order to measure scattering, it is necessary to measure both total spherical scatter (TSS) and scattering anisotropy (BSDF: bidirectional scatter distribution function).

In the field of optical measurement of scattered light from a sample, a scatterometer using a hemispheroidal mirror is known. A scatterometer using an integrating sphere and a scatterometer using a gonioreflectometer are also known. A scatterometer using an imaging hemisphere and a scatterometer using two ellipsoidal mirrors (also called "seagull-like scatterometer") (see U.S. Pat. No. 5,210,418) are also known.

The present inventor suggested a double ellipsoidal optical system structure and developed an optical characteristic measuring apparatus. The present inventor already developed an apparatus using an optical system using a double elliptical cylindrical mirror (see Japanese Patent Application Laid-Open Publication No. 2004-257956). In addition, the present inventor developed an apparatus for measuring absolute reflectance and absolute transmittance using an optical system constituted by combining two ellipsoidal mirrors, not by combining elliptical cylinders (see Japanese Patent Application Laid-Open Publication No. 2004-45065 and Japanese Patent Application Laid-Open Publication No. 2006-234681). Those apparatuses are each provided with a double ellipsoidal mirror composed of two spheroidal mirrors, and two beam switching mirrors and a sample are disposed at each focal point.

Furthermore, the present inventor developed an apparatus capable of rotating by a predetermine angle a light-receiving ellipsoidal mirror constituted by a double ellipsoidal optical system, and rotating by a small angle a beam switching mirror located at a focal point of the ellipsoidal mirror, and measured anisotropy of scattered light (see Kawate E., "Measurement method of optical scatter using a STAR GEM as a scatterometer" In proceedings of the SPIE, vol. 7065, 2008, 706515-1-706515-9 and FIG. 14 in Japanese Patent Application Laid-Open Publication No. 2010-276363). The double ellipsoidal optical system has a structure in which one focal point of the light-entering ellipsoidal mirror E1 and one focal point of the light-receiving ellipsoidal mirror E2 are used as a common focal point F0, and the remaining focal points of the ellipsoidal mirrors E1 and E2 are defined as F1 and F2, respectively, these three focal points F0, F1, and F2 are aligned with each other.

In addition, the present inventor developed an apparatus which rotates by a predetermined angle a light-receiving ellipsoidal mirror constituted by a double ellipsoidal optical system, and detects scattered light collected on a focal point of the rotated ellipsoidal mirror, thereby making it possible to measure total spherical scatter of a sample (see Japanese Patent Application Laid-Open Publication No. 2010-276363). In Japanese Patent Application Laid-Open Publication No. 2010-276363, first and second ellipsoidal mirrors constituting a double ellipsoidal optical system each has a structure made from a plate-like member or belt-shape member, which has a predetermined thickness (see FIG. 2 Japanese Patent Application Laid-Open Publication No. 2010-276363).

SUMMARY

Scattering quantities to be measured by the scatterometer includes the following quantities. In light scattering from a sample, light reflected from or transmitted through a sample is distributed on each a hemispherical surface. At this time, there are two important measurements: (1) by comparing a reflected light total quantity or a transmitted light total quantity to the hemispherical surface with a preliminarily-measured total background light quantity, a hemisphere total reflectance or a hemisphere total transmittance being obtained; and (2) a measurement of how the reflected light or the transmitted light is distributed on each hemispherical surface, that is, light distribution measurement (bidirectional reflectance distribution function or bidirectional transmittance distribution function).

A conventional scatterometer using a hemispheroidal mirror is used for a method to measure hemisphere total reflectance. This scatterometer was researched and developed until the 1980's, but was not put into practical use. The primary reason was that an integrating sphere, which was competing technology, was advanced by the development of high diffuse reflective material constituting an inner wall of the integrating sphere, and was put into practical use not only in an ultraviolet/visible region but also in an infrared region. The second reason was that this hemispheroidal mirror had two focal points, and reflectance of the sample was measured with the sample disposed at one focal point and a detector at the other focal point. Reflected light from the sample is reflected by the ellipsoidal mirror and focused on the detector, but not all incident light cannot be absorbed by the detector, so that reflected light from the detector is reflected again by the ellipsoidal mirror back to the sample. This occurs repeatedly, and thereby causes the problem that measured reflectance of the sample become larger than an actual value.

A conventional scatterometer using an integrating sphere is used for measuring quantitative hemisphere total reflectance (transmittance), and is now a mainstream of measurement in this field. However, this scatterometer has the problem that light distribution cannot be measured (see FIG. 16 in Japanese Patent Application Laid-Open Publication No. 2010-276363).

A conventional scatterometer using a gonioreflectometer is used for measuring light distribution (BSDF), and is now a mainstream of measurement in this field. However, a detector has to be scanned in 4π space, and therefore there is the problem that a set of measurements takes a long time. In principle, from data on light distribution measured at each point of the 4π space, hemisphere total reflectance and hemispherical total transmittance can be obtained (see FIG. 17 in Japanese Patent Application Laid-Open Publication No. 2010-276363).

A conventional scatterometer using an imaging hemisphere is used for measuring scattered light distribution using a CCD camera (light distribution measurement). This principle is shown in FIG. 26. A sample is placed at the center of the hemisphere, and incident light is caused to fall on the sample, as shown in FIG. 26. A fraction of diffusely-reflected light from the sample, which is reflected by a convex mirror disposed in the vicinity of the sample, falls on the CCD camera disposed outside the hemisphere. Since an inner face of the hemisphere is composed of a diffusely-reflective material and the reflectance thereof is suppressed to about 20%, analysis is made on the assumption that multiple reflections in the integrating hemisphere can be ignored. Measurement time is about 10 seconds. However, since this measuring method includes many assumptions, it impossible to perform an exact quantitative measurement.

A conventional scatterometer using two ellipsoidal mirrors (see U.S. Pat. No. 5,210,418) has a structure in which the two ellipsoidal mirrors are disposed at positions like wings of a seagull, a sample is disposed at a common focal point of the two ellipsoidal mirrors, and two fixed mirrors are disposed at two remaining focal points, respectively. In this structure, absolute reflectance measurement is impossible, only relative reflectance can be measured, and transmittance measurement is also impossible. Also regarding diffuse reflection measurement, only scattered light incident on one ellipsoidal surface can be measured, but there is the problem that quantitative measurement is impossible.

A conventional scatterometer (see Japanese Patent Application Laid-Open Publication No. 2010-276363) which rotates a light-receiving ellipsoidal mirror to perform measurement, and which was developed by the present inventor, can perform three measurements: hemisphere total reflectance, hemispherical total transmittance, and light distribution measurement. However, it was found that there are two problems to be solved. This scatterometer can shorten the time to measure light distribution as compared with a gonioreflectometer, but the measurement time is longer than in the case of an imaging hemisphere or the like. In order to measure hemisphere total reflectance (transmittance), it is necessary to integrate a quantity measured at each angle of rotation, but quantitative analysis is difficult.

The present invention is intended to solve these problems, and it is an object of the present invention to measure hemisphere total reflectance and/or hemispherical total transmittance, and light distribution (bidirectional reflectance distribution function or bidirectional transmittance distribution function) efficiently and in a short time, and to achieve high precision in quantitative measurement.

The present inventors have completed the present invention by improving, in an apparatus provided with the double ellipsoidal optical system, each shape of first and second ellipsoidal mirrors constituting the double ellipsoidal optical system, in such a manner that the first ellipsoidal mirror is composed of a strip of a ellipsoidal mirror having a shape obtained by cutting into a belt shape, and the second ellipsoidal mirror is composed of a partial body of a ellipsoidal mirror obtained by cutting into four parts, for example, quarters or eight parts. Measuring objects of the present invention are the following quantities:

(1) Hemisphere total transmittance and hemisphere total reflectance of a polished surface or a scattering surface;
(2) Light distribution of a polished surface or a scattering surface (bidirectional transmittance distribution function and bidirectional reflectance distribution function); and
(3) Spatial distribution of luminescence (light distribution) and total amount of luminescence from a luminous body such as LED.

In order to achieve the above objects, the present invention has the following features.

An optical characteristic measuring apparatus according to the present invention, for measuring scattered light from an object, comprises: a double ellipsoidal optical system composed of a partial ellipsoidal mirror and a belt-shape ellipsoidal mirror, and a hemispherical detection optical system, wherein the partial ellipsoidal mirror has, at least, a structure cut along a plane passing through an axis of the double ellipsoidal optical system and a plane perpendicular to the axis and passing through a common focal point, and wherein the hemispherical detection optical system is disposed at a position of a focal point of the partial ellipsoidal mirror. In the optical characteristic measuring apparatus according to the present invention, it is preferred that the hemispherical detection optical system be provided with a hemispherical lens, and the hemispherical lens be disposed so that the center of the hemispherical lens coincides with the position of the focal point of the partial ellipsoidal mirror. In the optical characteristic measuring apparatus according to the present invention, the hemispherical detection optical system may be provided with a tapered optical fiber which is disposed so that a large-diameter side end face of the optical fiber coincides with the position of a focal point of the hemispherical lens. In the optical characteristic measuring apparatus according to the present invention, it is preferred that the hemispherical detection optical system be provided with a rotational parabolic mirror which is disposed so that a focal point of the rotational parabolic mirror coincides with the position of the focal point of the partial ellipsoidal mirror. In the optical characteristic measuring apparatus according to the present invention, it is preferred that the hemispherical detection optical system be provided with a reflective surface mirror and a photodetector, and light from the rotational parabolic mirror be measured by the photodetector via the reflective surface mirror. In the optical characteristic measuring apparatus according to the present invention, it is preferred that the hemispherical detection optical system be provided with a convex lens and a photodetector, and light from the hemispherical lens or the rotational parabolic mirror be measured by the photodetector via the convex lens. In the optical characteristic measuring apparatus according to the present invention, the hemispherical detection optical system may be provided with a CCD camera as a photodetector.

In the optical characteristic measuring apparatus according to the present invention, the partial ellipsoidal mirror is a quarter ellipsoidal mirror or an octantal ellipsoidal mirror.

The double ellipsoidal optical system is an optical system in which one of focal points of the first ellipsoidal mirror and one of focal points of the second ellipsoidal mirror are coupled as a common focal point, and three focal points thus obtained exist along an axis.

The optical characteristic measuring apparatus of the present invention is provided with a reflective plate also called "beam switching mirror" at a focal point of the belt-shape light-entering ellipsoidal mirror, and an object to be measured (sample) is disposed at the common focal point, and the hemispherical detection optical system is disposed at the focal point of the partial ellipsoidal mirror.

The "hemispherical detection optical system" means an optical system capable of detecting all light reflected by a hemispherical mirrored surface and collected simultaneously. Examples of the hemispherical detection optical system include (1) a hemispherical lens, a tapered fiber, and a CCD camera, (2) a hemispherical lens, a tapered fiber, and a photo diode detector, (3) a hemispherical lens, a convex lens system, and a CCD camera, (4) a hemispherical lens, a convex lens system, and a photo diode detector, (5) a rotational parabolic mirror, a convex lens system, and a CCD camera, (6) a rotational parabolic mirror, a convex lens system, and a photo diode detector, (7) a rotational parabolic mirror, a reflective surface mirror, and a CCD camera, and (8) a rotational parabolic mirror, a reflective surface mirror, and a photo diode detector, and the like. Here, the "reflective surface mirror" is a term representing both a parabolic mirror and an ellipsoidal mirror. If the partial ellipsoidal mirror is a quarter ellipsoidal mirror, by using a hemispherical detection optical system, it is possible to simultaneously detect light reflected by the quarter ellipsoidal mirror. Alternatively, if the partial ellipsoidal mirror is an octantal ellipsoidal mirror, by using a hemispherical detection optical system, it is possible to simultaneously detect light reflected by the octantal ellipsoidal mirror.

While a conventional imaging hemisphere optical system or seagull-like scatterometer can measure only diffuse reflection, the present invention can measure not only reflectance but also transmittance simultaneously, by using the double ellipsoidal optical system composed of the partial ellipsoidal mirror and the belt-shape ellipsoidal mirror. Furthermore, while a conventional hemispheroidal mirror has the problem of multiple reflection, the present invention can reduce multiple reflection since the light-entering ellipsoidal mirror is the belt-shape ellipsoidal mirror having a small reflective area. Furthermore, by disposing a light source outside the belt-shape ellipsoidal mirror in such a manner that light is introduced into this ellipsoidal mirror through an incident through hole of this ellipsoidal mirror, a large effect of reducing multiple reflection is produced. In addition, in the present invention, since the belt-shape ellipsoidal mirror is used, an incident angle on the sample can be changed. In addition, if the sample is not diffusely-reflective (transmissive) (such as flat mirror or window glass), absolute specular reflectance and absolute specular transmittance can be measured.

In the present invention, since the partial ellipsoidal mirror has a structure cut along a plane passing through an axis of a double ellipsoidal optical system and along a plane perpendicular to the axis and passing through the common focal point, it is possible to avoid its multiple reflectance.

In the present invention, since the double ellipsoidal optical system composed of the partial ellipsoidal mirror and the belt-shape ellipsoidal mirror is used, the hemispherical detection optical system is disposed at the focal point of the partial ellipsoidal mirror, and light reflected by the hemisphere front face can be detected simultaneously, so that hemispherical total reflectance or hemispherical total transmittance, and light distribution measurement (bidirectional reflectance distribution function or bidirectional transmittance distribution function) can be efficiently measured in a short time.

In addition, in the present invention, absolute measurement, such as absolute reflectance and absolute transmittance of a sample having a diffusive surface, can be performed with high precision. In the present invention, a sample is disposed at the common focal point, the sample is irradiated with excitation light from the side of the belt-shape ellipsoidal mirror, and luminescence from the sample is radiated over an entire space (4π steradians), but light incident on the quarter ellipsoidal mirror (π steradians) can be collected by the hemispherical detection optical system, introduced into the detector, and analyzed.

In the present invention, when a light-emitting diode is placed at the common focal point, instead of a sample, quantitative measurement of spatial distribution and total amount of luminescence of radiated light from the light-emitting diode can also be performed by using the quarter ellipsoidal mirror.

If a CCD camera is directly disposed at the focal point (F2) of the quarter ellipsoidal mirror, light allowed to fall on the camera is limited within a solid angle of about one sixteenth of a hemisphere (2π steradians) since an imaging surface of the camera is about 10-mm recessed in a casing of the camera. On the other hand, in the present invention, since a hemispherical lens is used, light incident on the bottom surface of the hemispherical lens from a solid angle of the hemispherical surface (2π steradians) can be collected into a solid angle of one seventh of the hemisphere when the light exits from the hemispherical lens. However, a beam exiting from the hemispherical lens with the solid angle of one seventh of this hemisphere is about 10 mm in diameter, which is larger than the size of the imaging surface of the CCD camera (for example, 7 mm in length and 5.3 mm in width), and therefore all light cannot be taken into the CCD camera. In the present invention, it has been found that light emitted from the hemispherical lens forms an image at a distance approximately equal to a radius from the top of the lens. The diameter of a beam at this position is about 10 mm, which is the above-mentioned distance, and therefore, disposing an end face on a large-diameter side (20 mm in diameter) of a tapered optical fiber at this position, all light can be taken into the fiber. The diameter of an end face on a small-diameter side of this fiber taper is about 6 mm, which is smaller than the imaging surface of the CCD camera, and therefore all light exiting from the fiber can fall on the CCD camera. It should be noted that each numerical value is shown by way of example for description, and the same advantageous effect can be obtained independently of the numerical values.

In the present invention, a combination of a rotational parabolic mirror and a reflective surface mirror (a parabolic mirror or an ellipsoidal mirror) makes it possible to match light diffusing over a solid angle of the hemisphere with a light-receiving solid angle of the CCD camera. In the hemispherical detection optical system using a hemispherical lens or the like, since the refraction index of the lens or the like depends on wavelength, it is necessary to change the material of the hemispherical lens or the fiber taper in the middle, in order to measure a wide wavelength region. On the other hand, when a rotational parabolic mirror and a reflective surface mirror are used in combination, it is reflective optical system and there is no wavelength dependence, so that a wide wavelength region of ultraviolet, visible, and infrared regions can be covered by a single hemispherical detection optical system.

DETAILED DESCRIPTION

Hereinafter, embodiments of the present invention will be described in detail with reference to the accompanying drawings.

First Embodiment

Figure 1:
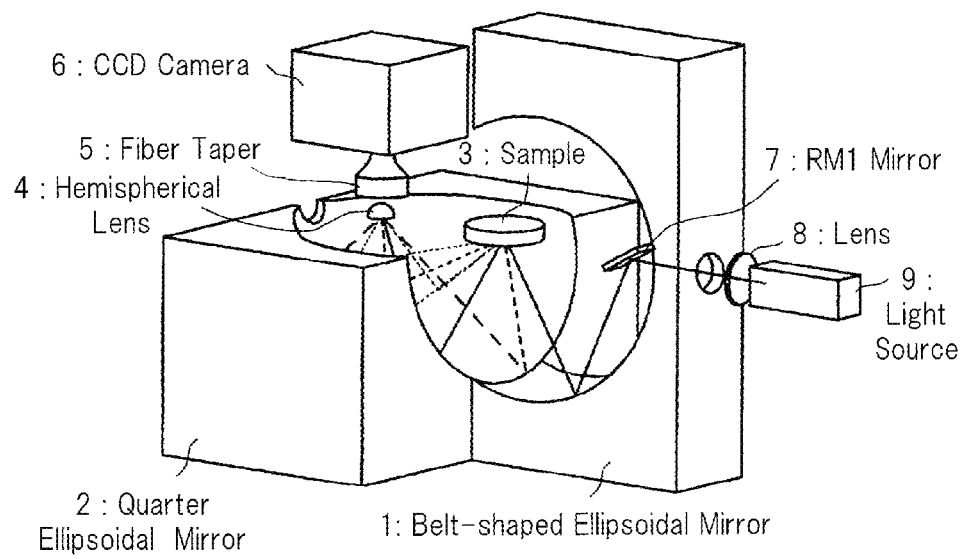
FIG. 1 is a view showing a reflection measuring arrangement in an optical characteristic measuring apparatus according to a first embodiment.
Figure 2:
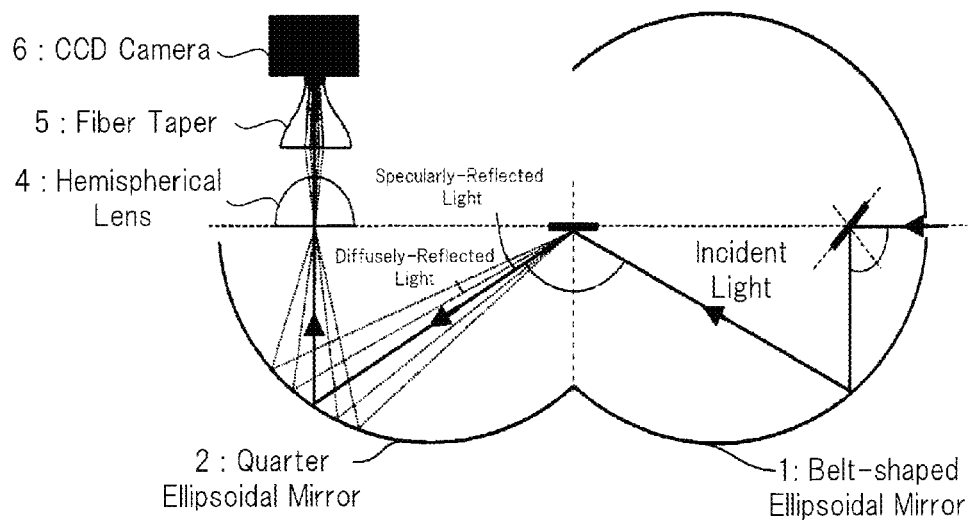
FIG. 2 is a cross sectional view showing the optical characteristic measuring apparatus according to the first embodiment.
Figure 3:
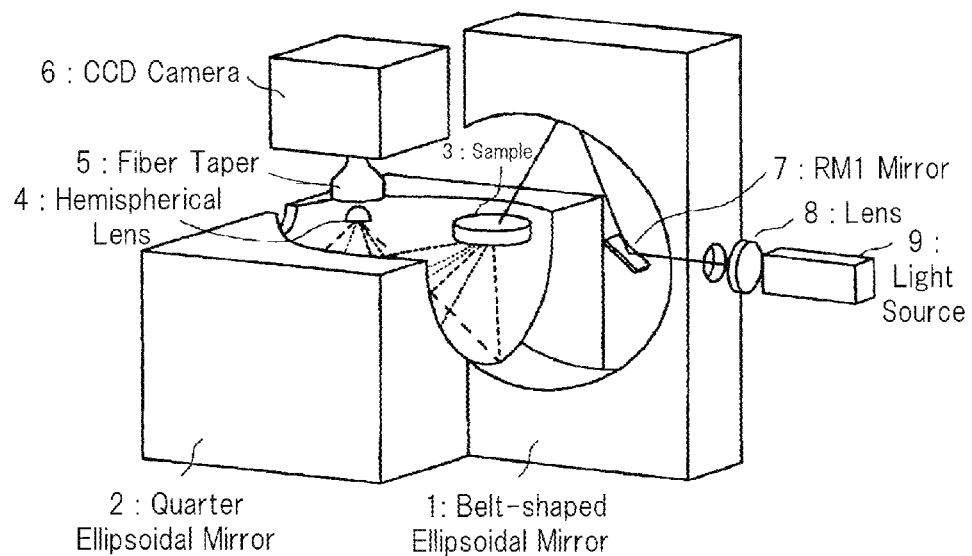
FIG. 3 is a view showing a transmission measuring arrangement in the optical characteristic measuring apparatus according to the first embodiment.
Figure 4:
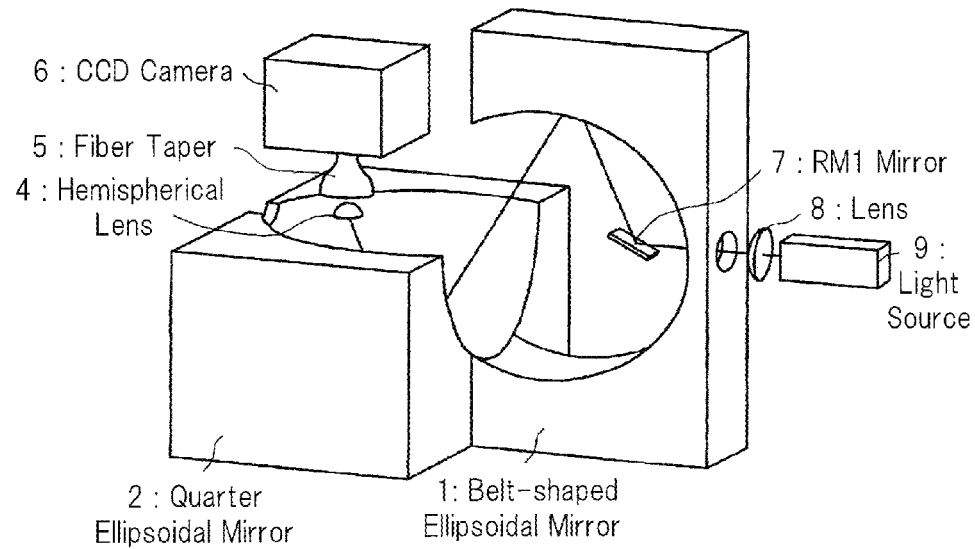
FIG. 4 is a view showing a background measuring arrangement in the optical characteristic measuring apparatus according to the first embodiment.
Figure 5:
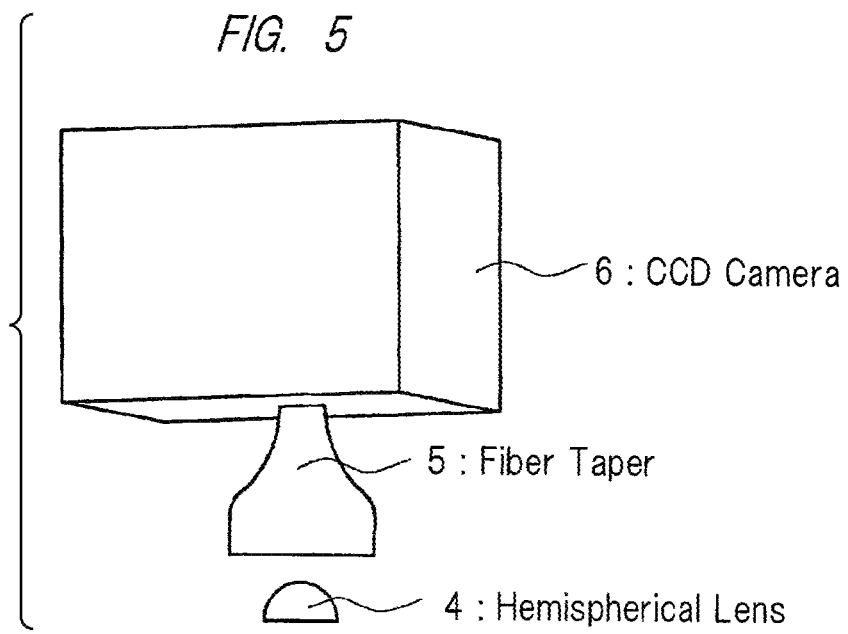
FIG. 5 is a view showing a hemispherical detection optical system in the first embodiment.
Figure 6:
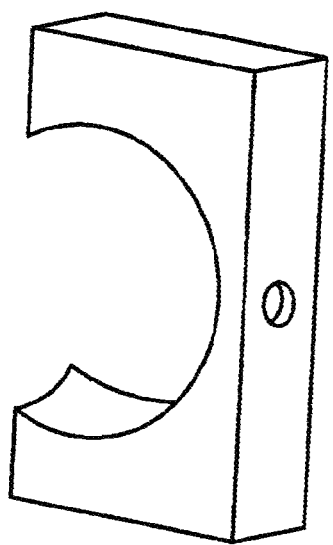
FIG. 6 is a view showing a belt-shape ellipsoidal mirror in the first embodiment.
Figure 7:
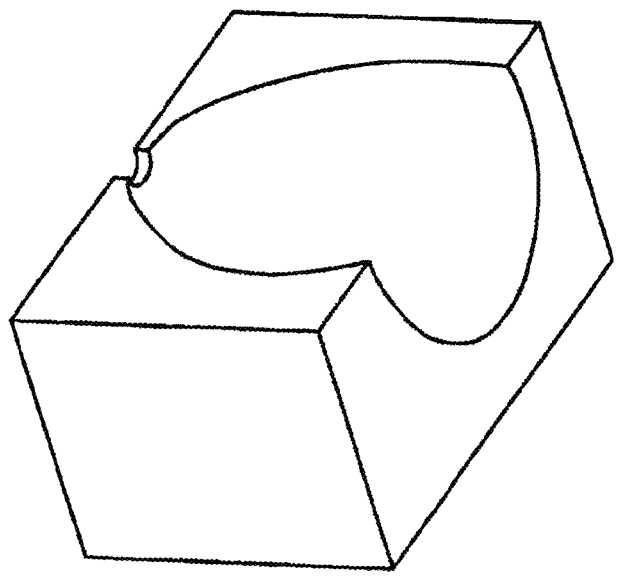
FIG. 7 is a view showing a quarter ellipsoidal mirror in the first embodiment.
Figure 8:
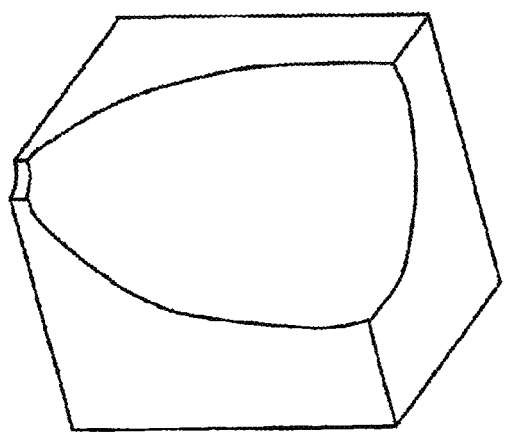
FIG. 8 is a view showing an octantal ellipsoidal mirror in the first embodiment.
Figure 9:
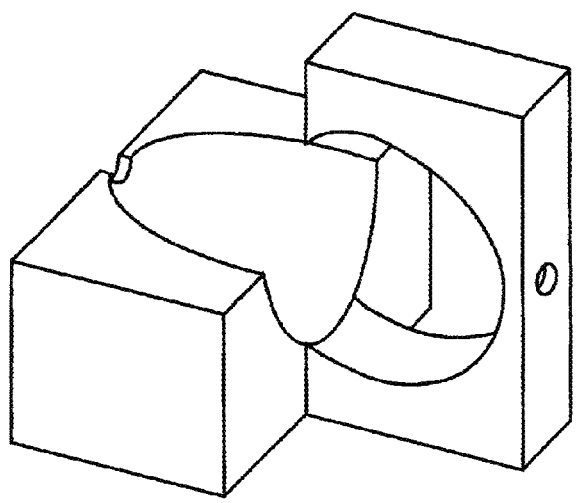
FIG. 9 is a view explaining the arrangement of the belt-shape ellipsoidal mirror in the first embodiment.
Figure 10:
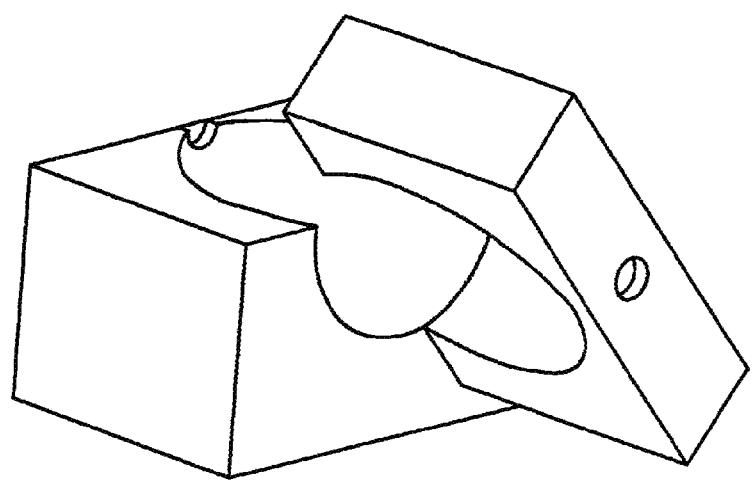
FIG. 10 is a view explaining the arrangement of the belt-shape ellipsoidal mirror in the first embodiment.
Figure 11:
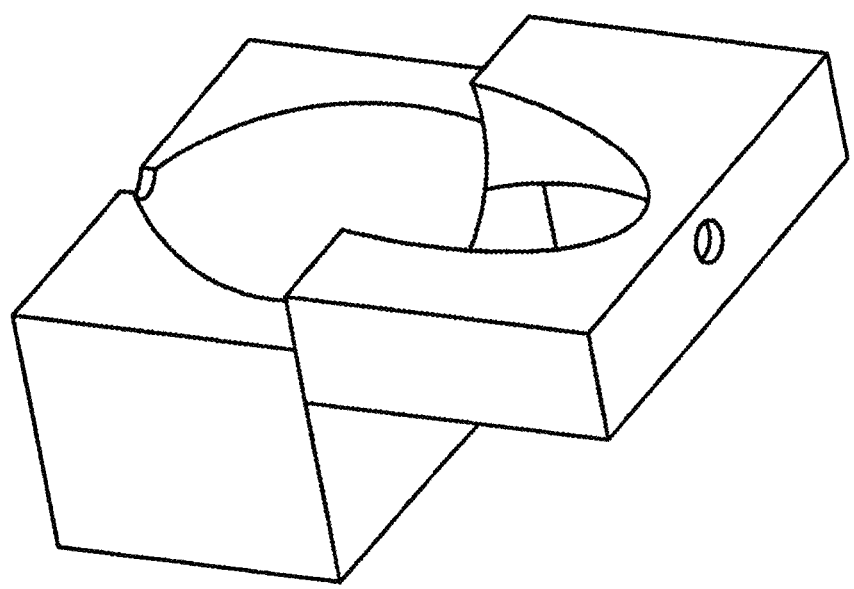
FIG. 11 is a view explaining the arrangement of the belt-shape ellipsoidal mirror in the first embodiment.

A representative structure, an evaluation result and the like of an optical characteristic measuring apparatus for measuring scattered light from a sample will be described below. FIG. 1 is a perspective view showing a representative structure of a first embodiment and showing a reflection measuring arrangement. FIG. 2 is a cross-sectional view schematically showing the apparatus of FIG. 1 and showing a reflection measuring mode. FIG. 3 is a view showing a transmission measuring arrangement. FIG. 4 is a view showing a background measuring arrangement. FIG. 5 is a view showing a hemispherical detection optical system. FIG. 6 is a view showing a belt-shape ellipsoidal mirror. FIG. 7 is a view showing a quarter ellipsoidal mirror. FIG. 8 is a view showing an octantal ellipsoidal mirror. FIGS. 9, 10, and 11 are views showing the rotation of the belt-shape ellipsoidal mirror.

Firstly, as a precondition for the present invention, a double ellipsoidal optical system will be described in detail. The double ellipsoidal optical system is constituted so that two ellipsoidal mirrors are arranged adjacently, their rotation axes being axially aligned with each other, and these ellipsoidal mirrors are formed by cutting along planes perpendicular to their rotation axes and including focal points close to each other, and connecting them so as to match their cut planes. Each of the ellipsoidal mirrors has a polished inner surface. One focal point of the first light-entering ellipsoidal mirror and one focal point of the second light-receiving ellipsoidal mirror are positioned as a common focal point, and three focal points composed of the common focal point and two remaining focal points of the two ellipsoidal mirrors are aligned in a straight line (the dotted line in FIG. 2). The straight line connecting the three focal points is called "axis of the double ellipsoidal mirror". This straight line axially aligns with the rotation axes of the two ellipsoidal mirrors, and is also the rotation axis of the double ellipsoidal mirror.

In the apparatus according to the first embodiment, as shown in FIG. 1, one ellipsoidal mirror (first ellipsoidal mirror) of the double ellipsoidal optical system structure is composed of a belt-shape ellipsoidal mirror 1, the other ellipsoidal mirror (second ellipsoidal mirror) is composed of a quarter ellipsoidal mirror 2, and a structure to detect scattered light focused on the focal point of the second ellipsoidal mirror is provided.

Figure 12:
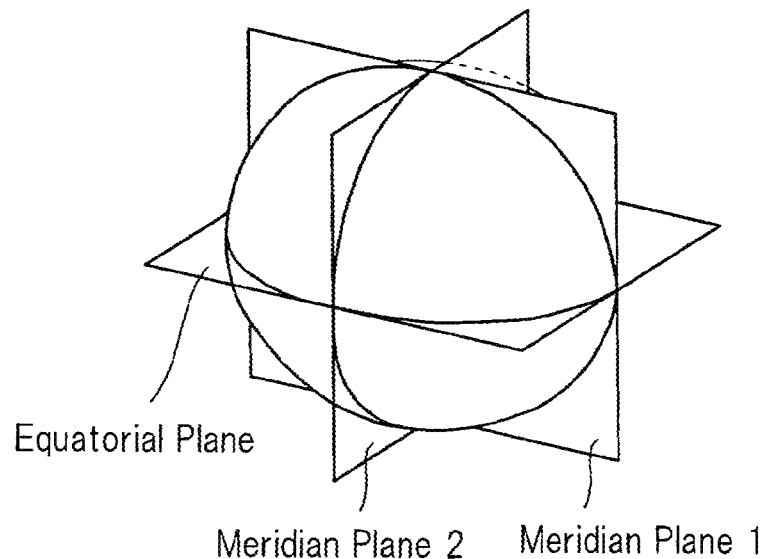
FIG. 12 is a view explaining an equatorial plane and the like of the ellipsoidal surface.
Figure 13:
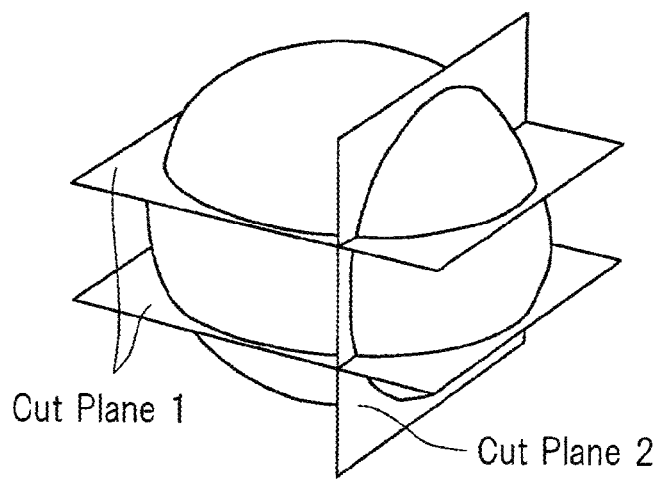
FIG. 13 is a view explaining cut planes of an ellipsoid.

The belt-shape ellipsoidal mirror 1 and the quarter ellipsoidal mirror 2 will be described below with reference to FIGS. 12 and 13. FIGS. 12 and 13 are views explaining cut planes of ellipsoidal surfaces (the first and second ellipsoidal mirrors). In FIG. 12, a plane exactly intermediate between the north pole and the south pole of the ellipsoidal surface is called "equatorial plane". A plane perpendicular to the equatorial plane, passing through the north pole and the south pole, and including the longitudinal axis is called "meridian plane 1". A plane perpendicular to the equatorial plane, passing through the north pole and the south pole, including only the short axis is called "meridian plane 2". In FIG. 13, cut planes 1 are planes separated vertically at the same distance (for example, 20 mm) from the equatorial plane. A cut plane 2 is a plane perpendicular to the equatorial plane and passing through one focal point of the ellipsoid.

A belt-shape ellipsoid is a solid left after the ellipsoid is cut along two planes of the cut plane 1 and the cut plane 2.

A quarter ellipsoid is a portion which is left after the ellipsoid is cut along the equatorial plane and the cut plane 2. The volume of the quarter ellipsoid is not exactly a quarter of the volume of the ellipsoid, but is called "quarter ellipsoid" in the present invention.

An octantal ellipsoid is a solid left after the ellipsoid is cut along the equatorial plane, the meridian plane 1, and the cut plane 2. The volume of the octantal ellipsoid is not exactly one eighth of the volume of the ellipsoid, either, but is called "octantal ellipsoid" in the present invention.

Incidentally, a conventional hemispheroid is a solid left after the ellipsoid is cut along the equatorial plane.

The apparatus according to the first embodiment is provided with: a hemispherical lens 4; a tapered optical fiber (also called "fiber taper") 5; a CCD camera 6; a beam switching mirror (RM1 mirror) 7; a lens 8; and a light source 9. The RM1 mirror 7 is disposed at the focal point of the first ellipsoidal mirror, a sample (an object to be measured) 3 is placed at the common focal point, and the hemispherical lens 4 is disposed at the focal point of the second ellipsoidal mirror. A through hole of incident light is formed at an intersection of the axis of the double ellipsoidal mirror with the first ellipsoidal mirror.

Figure 14:
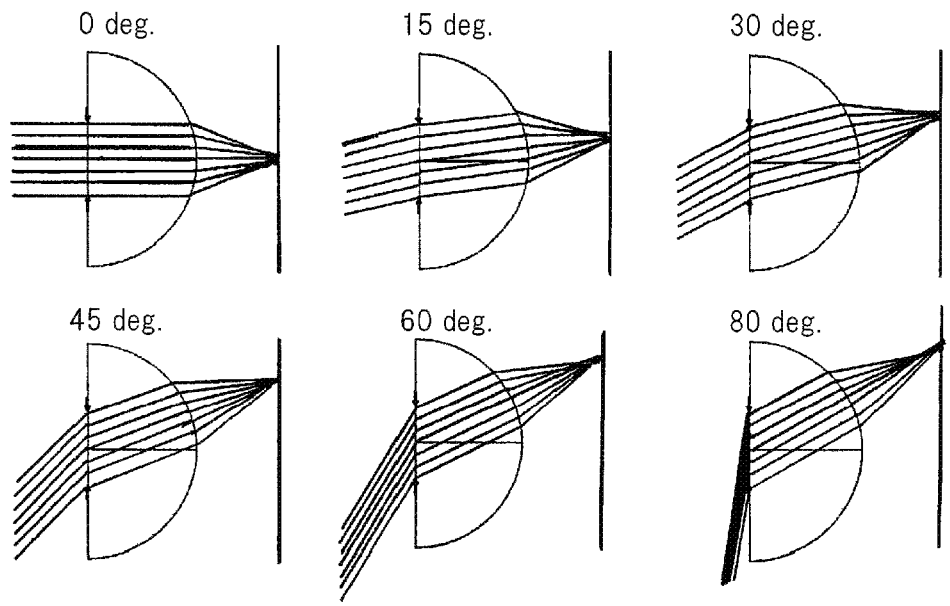
FIG. 14 is a view showing light passing through a hemispherical lens.
Figure 15:
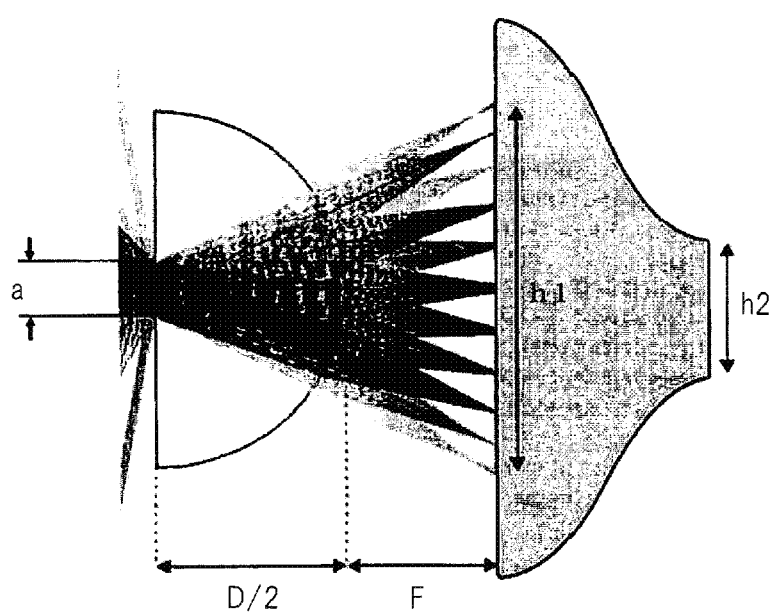
FIG. 15 is a view showing a hemispherical detection optical system using the hemispherical lens and a fiber taper.

The reflection measurement mode in the reflection measurement arrangement in FIG. 1 will be described below. When light from the light source 9 (a laser source, a spectrophotometer, or the like) is taken into the double ellipsoidal mirror through the lens 8 and the incident through hole, the light reaches the bean switching mirror (RM1 mirror) 7. The light reflected by the beam switching mirror (RM1 mirror) 7 is further reflected by the first ellipsoidal mirror (belt-shape ellipsoidal mirror 1) to fall on the sample 3 at the common focal point. The light reflected by the sample 3 is reflected by the second ellipsoidal mirror (the quarter ellipsoidal mirror 2) to concentrate on the focal point. When the center of the hemispherical lens is disposed so as to coincide with this focal point, all light incident on a flat surface of the hemispherical lens is refracted by an angle depending on the refractive index of material of the hemispherical lens. Furthermore, the characteristic of this hemispherical lens causes parallel light rays falling from an arbitrary direction on the side of the quarter ellipsoidal mirror to focus on a certain distance depending on the radius of the lens, the refractive index of the material, and the incident angle to the hemispherical lens. Results of simulations using a ray-tracing software are shown in FIGS. 14 and 15. In the case of a hemispherical lens having a refractive index of 2 and a diameter of 10 mm (D in FIG. 15), a distance from the top of the lens to a light collection point (F in FIG. 15) is about 4 mm. At this light collection point, an end face on a large-aperture side of the tapered optical fiber (also called fiber taper) 5 is disposed. A CCD camera image can be sharpened by disposing an end face on a small-aperture side of the tapered optical fiber in the vicinity of a pixel surface of the CCD camera 6.

The belt-shape ellipsoidal mirror 1 will be further described below. While a conventional imaging hemisphere optical system or seagull-like scatterometer can measure reflectance but cannot measure transmittance because of its structure, the apparatus according to the present invention uses a belt-shape ellipsoidal mirror on a light-entering side, thereby making it possible to measure not only reflectance but also transmittance simultaneously.

In addition, a conventional hemispheroidal mirror has the problem of multiple reflection, but the present invention can reduce multiple reflection since the light-entering ellipsoidal mirror is composed of a belt-shape ellipsoidal mirror having a small reflective area, furthermore a light source is disposed outside the belt-shape ellipsoidal mirror, and light is introduced into this ellipsoidal mirror through an incident through hole in this ellipsoidal mirror.

Furthermore, in the present invention, the angle of incidence on the sample can be changed since the belt-shape ellipsoidal mirror is used. Further, in the case of a non-diffusely-reflective (transmissive) sample (an aluminum flat mirror or a window glass), absolute reflectance and absolute transmittance can be measured by using the idea of a symmetric X-shaped optical system (Japanese Patent No. 3470267) (an optical system where a light path of reflection measurement and a light path of background measurement are created so as to overlap with each other anywhere in a space so that light losses at optical elements in the light paths can compensate each other. For this purpose, actually reflectance measurement is performed twice, and background measurement is also performed twice.).

The quarter ellipsoidal mirror 2 will be further described below. In the present invention, since a quarter ellipsoidal mirror is used instead of a hemispheroidal mirror, it is possible to decrease multiple reflection. However, a space which can be measured by the quarter ellipsoidal mirror is not a half space ($2\pi$ space) but a quarter space ($\pi$ space) at most.

An octantal ellipsoidal mirror may be used instead of the quarter ellipsoidal mirror. In the case of using the octantal ellipsoidal mirror to avoid multiple reflection, a maximum space which can be measured at a time is an octantal space.

A hemispherical detection optical system will be described below. FIG. 5 is a view showing a hemispherical detection optical system. In this embodiment, the hemispherical detection optical system is provided with: the hemispherical lens 4; the fiber taper 5; and the CCD camera 6. The fiber taper 5 is obtained by forming a tapered fiber bundle for transmitting an image, and is a high-resolution image transmitting apparatus having a function of enlarging or reducing an image from an incident plane by a predetermined magnification, and transmitting the image to the other end face.

In order to measure light from the entire hemispherical surface, the hemispherical detection optical system is disposed so that a detection system does not protrude into a space of the quarter ellipsoidal mirror 2. The hemispherical lens 4 and the fiber taper 5 perform a function exactly similar to a fisheye lens. The hemispherical detection optical system is disposed so that all light from the entire hemisphere surface can be collected, and so that collected light firstly falls on the hemispherical lens 4.

Light rays incident on the hemispherical lens will be described with reference to FIG. 14. FIG. 14 shows incident angles and imaging locations when parallel light rays are incident on a hemispherical lens of 10 mm in diameter having an aperture of 2 mm in diameter. As shown in FIG. 14, all light from the entire hemisphere can be collected.

FIG. 15 is a view explaining a relative positional relationship between the hemispherical lens and the fiber taper. A distance from the hemispherical lens to an imaging surface of the hemispherical lens depends on the refractive index and a radius of the hemispherical lens and the incident angle. When the refractive index is 2 and the radius is 5 mm, a distance from the top of the hemisphere to the imaging surface is about 4 mm. An incident surface of the fiber taper is disposed so as to coincide with the imaging surface. An aperture "a" (1.5 mm) is attached to the hemispherical lens (a diameter of 10 mm, a refractive index of 2), the large-diameter surface of the fiber taper (a diameter h1) is disposed at a total distance of D/2 (a radius of the hemispherical lend) and F (focal length) from the bottom surface of the hemispherical lens, and the small-diameter surface (a diameter h2) is caused to be in close contact with the pixel face of the CCD camera. Specifically, the imaging surface is a curved surface, but the fiber taper may be a flat surface, as shown in FIG. 15. Thus, regarding the fiber taper 5, it is preferred that one face of the fiber taper be disposed at the focal point of the hemispherical lens since the image at the focal point can be transmitted to the pixels of the CCD camera and therefore a sharper image can be obtained. However, one face of the fiber taper may be disposed at a location other than the focal point of the hemispherical lens.

Since the CCD camera 6 has the pixel surface in a recess of a casing, light can be efficiently collected by using the fiber taper 5. From the image of the CCD camera, information on light being distributed in a space (light distribution) can be obtained. Furthermore, a hemisphere total reflectance (transmittance) can be obtained by integrating the charge amounts of respective pixels of the CCD camera.

Next, a measuring method will be described. Background measurement is performed without the sample in the arrangement shown in FIG. 4. In the case of transmittance measurement shown in FIG. 3, when light from the light source 9 (light from a laser source or a spectrophotometer) is introduced into the double ellipsoidal mirror through the lens 8 and the incident through hole, the light reaches the beam switching mirror (RM1 mirror) 7 oriented in a direction shown in FIG. 3, which differs from the direction in the case of reflection measurement. The light reflected by the beam switching mirror (RM1 mirror) 7 is further reflected by the belt-shape ellipsoidal mirror 1, and falls on the sample 3 at the common focal point. The light transmitted through the sample 3 is reflected by the quarter ellipsoidal mirror 2 and concentrated on the focal point.

The incident angle on the sample 3 can be changed by rotating the beam switching mirror (RM1 mirror) 7 by a predetermined angle.

A measuring method to rotate the belt-shape ellipsoidal mirror and perform measurement will be described below with reference to FIGS. 9 to 11 and 16A to 18. The belt-shape ellipsoidal mirror is rotated in order to remedy the problem that the image formed by the hemispherical lens is more compressed in its outermost peripheral part in comparison with its central part. FIG. 9 schematically shows an arrangement in which the belt-shape ellipsoidal mirror is perpendicular to the equatorial plane of the quarter ellipsoidal mirror. FIG. 11 schematically shows an arrangement in which the belt-shape ellipsoidal mirror is at a horizontal position, and FIG. 10 schematically shows an arrangement in which the belt-shape ellipsoidal mirror is in the middle of rotation.

A method using at the first stage the hemispherical lens as a hemispherical detection optical system has the drawback that the image is made excessively small in its outermost peripheral part in comparison with its central part. In order to remedy this drawback, first, the belt-shape ellipsoidal mirror and the sample should be rotated correlatively. In practice, a complete quarter space image is obtained by synthesizing one image of the central part and three images of the peripheral part, the sample is rotated by 180 degrees about a Y-axis, and images are then taken four times in the procedure described above, and then synthesized. Thus, the remaining quarter space image is obtained. By synthesizing these two images, a half space ($2\pi$ space) can be measured.

Incidentally, here, an X-axis, a Y-axis, and a Z-axis have their coordinate origin at the common focal point, and are defined as follows. The x-axis is a line connecting the light source, the sample, and the bottom surface of the hemispherical lens (the dotted line in FIG. 2), and coincides with the rotation axis of the belt-shape ellipsoidal mirror. The y-axis is a perpendicular straight line passing through the origin (the broken line in FIG. 2). The z-axis is a line connecting edges cut at a right angle of the quarter ellipsoid, and is an axis perpendicular to the x-axis and the y-axis.

Figure 16A:
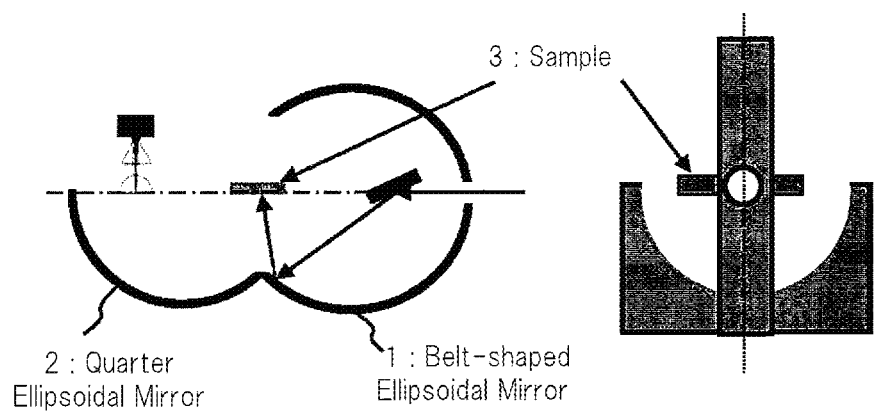
FIGS. 16A and 16B are views explaining a rotation of a sample in the first embodiment.
Figure 16B:
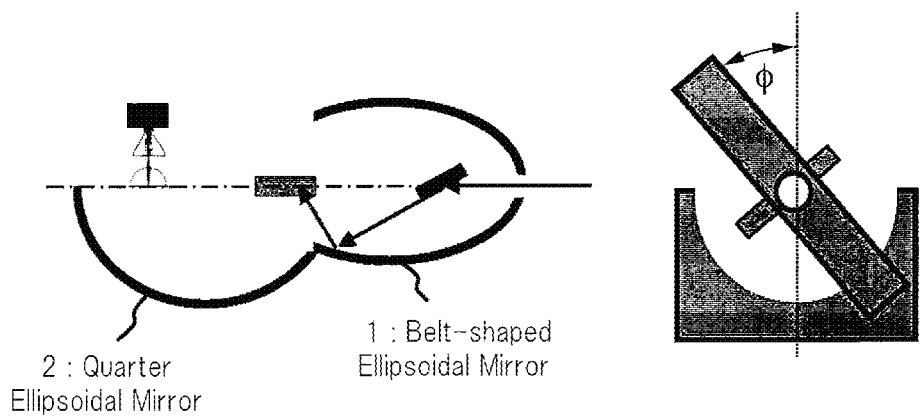
Figure 17A:
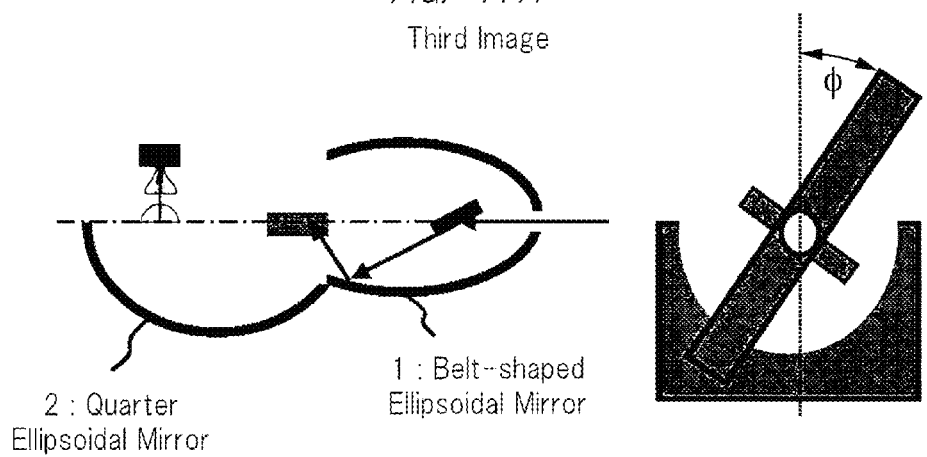
FIGS. 17A and 17B are views explaining a rotation of a sample in the first embodiment.
Figure 17B:
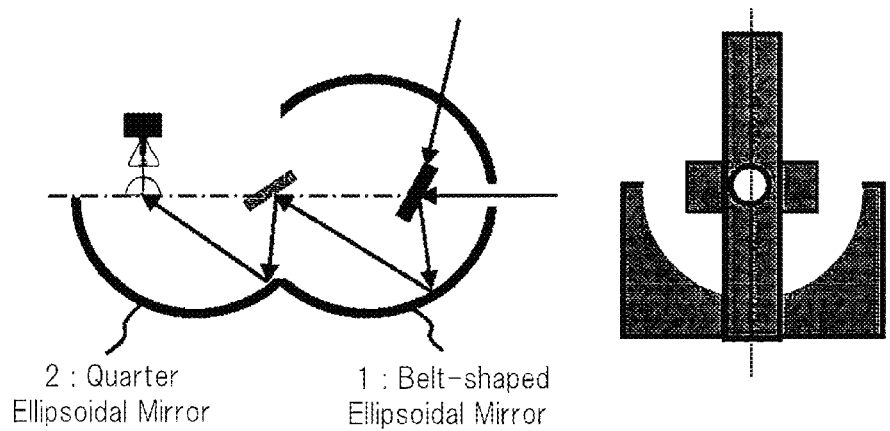
Figure 18:
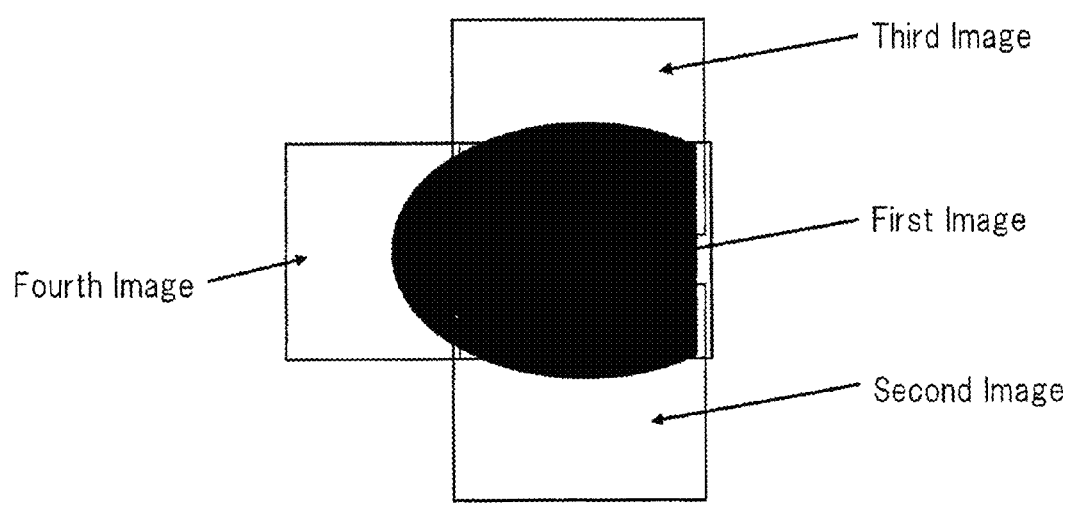
FIG. 18 is a view explaining a synthesized image in the first embodiment.

FIGS. 16A, 16B, 17A, 17B, and 18 show photographing and screen synthesis of the $\pi$ space by using the quarter ellipsoidal mirror. FIG. 16A shows a normal arrangement in the case of a first image. FIG. 16B shows an arrangement in the case of a second image, where the sample is rotated by an angle ø in a counterclockwise direction about the x-axis, and the belt-shape ellipsoidal mirror is also rotated by the same angle. FIG. 17A shows an arrangement in the case of a third image, where the sample is rotated by an angle ø in a clockwise direction about the x-axis, and the belt-shape ellipsoidal mirror is also rotated by the same angle. FIG. 17B shows an arrangement in the case of a fourth image, where the sample is rotated by an angle ø in a counterclockwise direction about the z-axis, and the RM1 mirror is also rotated by the same angle. FIG. 18 shows an aspect that the first to fourth images are synthesized to perform image synthesis of the sample.

Furthermore, it is possible to perform photographing and image synthesis of the $2\pi$ space by rotating the sample by 180 degrees and repeating the same measurements. That is, in order to measure reflected light or transmitted light from the same side surface of the sample as the belt-shape ellipsoidal mirror, the sample is rotated about the y-axis by 180 degrees, and the same measurements as those of FIGS. 16 and 17 are repeated. By synthesizing these eight images, an exact light distribution of the $2\pi$ space can be obtained.

Figure 19:
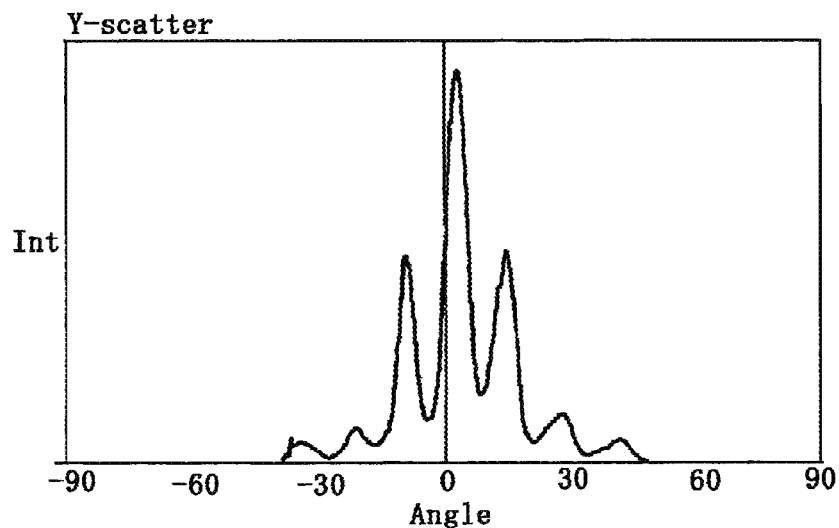
FIG. 19 is a graph showing a measurement result obtained by the optical characteristic measuring apparatus according to the first embodiment.

A measurement result obtained by using the apparatus according to the first embodiment is shown in FIG. 19. The light source was a He-Ne laser, a diffraction grating was used as the sample, the grating was irradiated with laser light, and diffusely-reflected light (to be exact, diffracted light) from the grating was measured. The horizontal axis in FIG. 19 indicates scattering angles, while the vertical axis indicates outputs measured by the CCD camera. By using the apparatus according to the first embodiment, it is found that a high-order diffraction image from the grating is measured with high precision.

Figure 20:
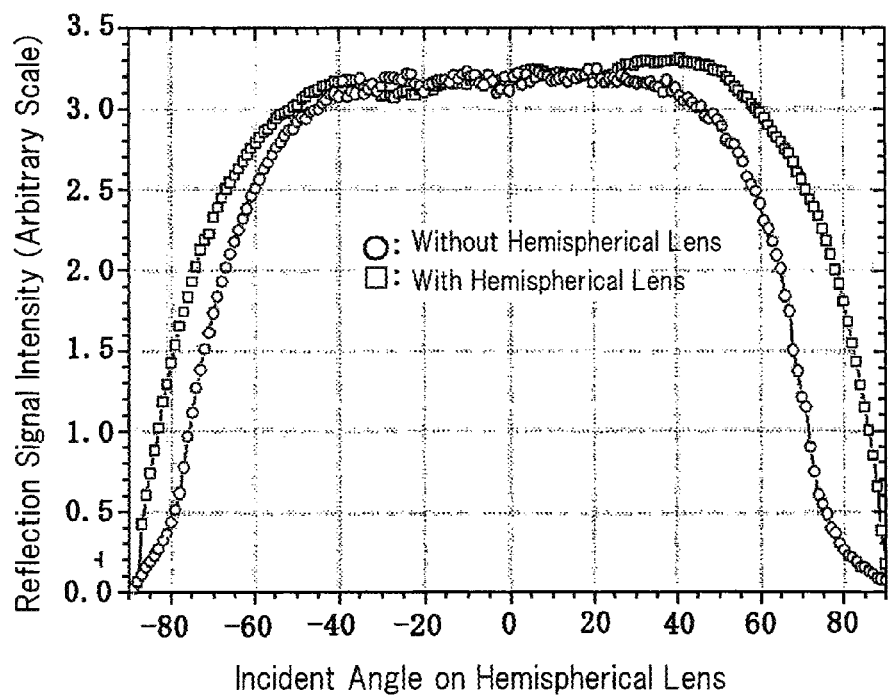
FIG. 20 is a graph showing an effect of the hemispherical lens of the optical characteristic measuring apparatus according to the first embodiment.

A measurement result of an effect of the hemispherical lens as a fisheye lens is shown below. FIG. 20 shows measurement results measured by the apparatus according to the first embodiment and an apparatus without a hemispherical lens. The horizontal axis indicates incident angles on the hemispherical mirror, while the vertical axis indicates reflection signal intensities. A circle denotes a signal intensity in the absence of the lens, while a square denotes a signal intensity in the presence of the lens. It should be noted that for comparison, normalization is performed at the peaks of signal intensity curves. The signal intensity curve in the presence of the lens is more swollen to right and left than that in the absence of the lens. This swell indicates the effect of the hemispherical lens as a fisheye lens.

Figure 21:
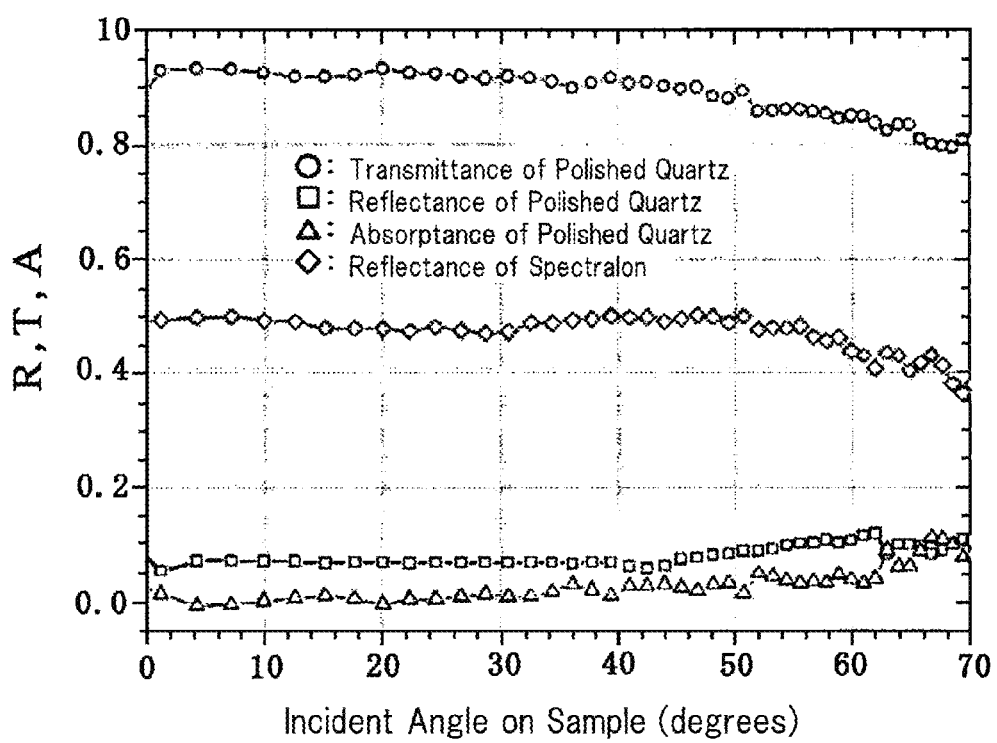
FIG. 21 is a graph showing a measurement result obtained by the optical characteristic measuring apparatus according to the first embodiment.

Using a polished parallel plate quartz sample and a Spectralon sample, diffuse reflectance, transmittance, and absorptance were measured. FIG. 21 shows the measurement results. The horizontal axis indicates incident angles (degrees) on the samples. The vertical axis indicates reflectance, transmittance, and absorptance (R, T, A). A circle indicates a transmittance of the polished quartz, a square indicates a reflectance of the polished quartz, a triangle indicates an absorptance of the polished quartz, a rhombus indicates a reflectance of the Spectralon. The polished parallel plate quartz has zero absorptance in this wavelength range (a wavelength of the He-Ne laser of 633 nm), and is therefore a material causing ideal specular reflection and specular transmission. The measurement results also show that in the range of small incident angles, the absorptance was approximately zero, and the reflectance and the transmittance agreed with also recommended values of a handbook. The Spectralon is an ideal perfectly-diffusing plate. The measurement result of reflectance of this sample was approximately 50% in the range of small incident angles. Considering that the space the quarter ellipsoidal mirror views is $\pi$, the total reflectance is 100%, that is, just twice 50%, which indicates good coincidence.

From the measurement results, it is found that by using the quarter ellipsoidal mirror, reflectance and transmittance can be measured with high precision.

In order to measure hemispherical total reflectance (transmittance), instead of the CCD camera, a photodetector such as a photodiode (silicon photo diode) or a photomultiplier tube, may be used.

Samples to be measured include various samples, such as carbon nanotube and micro lens. For example, since a spatial distribution of diffusely-reflected light is strained if a micro lens has a flaw, whether or not there is a strain can be determined in a measuring time of about 10 seconds.

Second Embodiment

Figure 22:
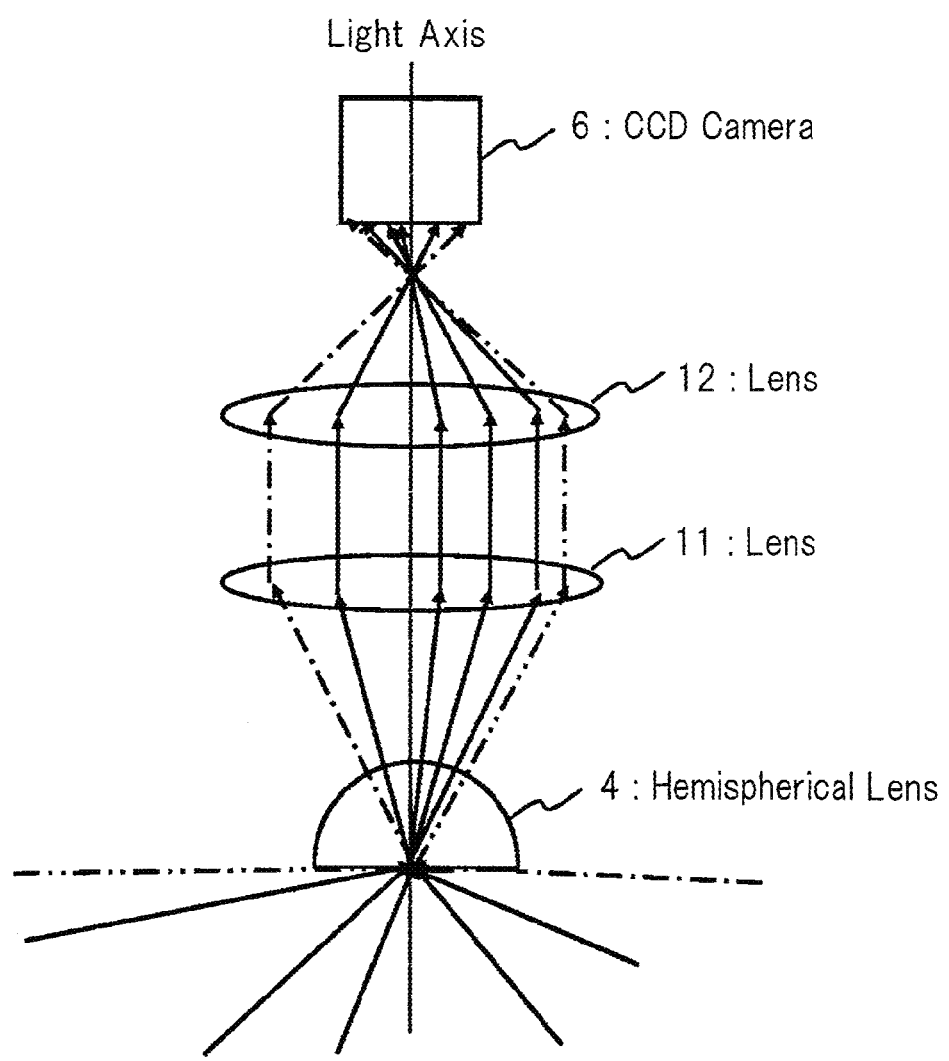
FIG. 22 is a view showing an optical characteristic measuring apparatus according to a second embodiment.

In the first embodiment, the example using a hemispherical lens, a fiber taper, and a CCD camera, and the example using a hemispherical lens, a fiber taper, and a photo diode detector, as a hemispherical detection optical system, are described. In a second embodiment, the example using a convex lens system instead of the fiber taper will be described with reference to FIG. 22. In FIG. 22, a point at which five solid lines, and a dashed-dotted line, and a dashed-two dotted line gather is a focal point F2 of the ellipsoidal mirror. The center of the hemispherical lens is disposed so as to coincide with the focal point F2 of the ellipsoidal mirror. In addition, the bottom surface of the hemispherical lens is disposed parallel to an edge face of the quarter ellipsoidal mirror. This prevents the hemispherical detection optical system from making a shadow inside the ellipsoidal mirror, and therefore the hemispherical lens can concentrate all light collected from the $2\pi$ space on the focal point F2.

The dashed-dotted line and the dashed-two dotted line represent light rays travelling substantially parallel to the bottom surface of the hemispherical lens, and gather at the focal point F2. A hemispherical detection optical system of the second embodiment is provided with a hemispherical lens 4, a convex lens system (a convex lens 11, a convex lens 12), and a CCD camera 6. Light concentrated on a focal point of the quarter ellipsoidal mirror from the $2\pi$ space falls on the hemispherical lens 4, and converged by the refraction index of the hemispherical lens when exiting from this lens. When the hemispherical lens has a refraction index n=2, light exiting from this lens is converged to 0.134×$2\pi$ (steradians). Since the incident light has $2\pi$ steradians at an incident time, beams in the hemispherical space are converged to 13.4% space.

The light passed through the hemispherical lens 4 is collimated by the convex lens 11, and then collected by the convex lens 12 in the convex lens system (the convex lens 11, the convex lens 12), and the CCD camera 6 is disposed in the vicinity of the focal point of the convex lens 12. By imaging the light from the entire hemispherical surface with the camera, an image of the entire hemispherical surface can be obtained. Therefore, it is possible to obtain a light distribution in a short time.

In order to measure hemisphere total reflectance, instead of the CCD camera 6, a photodetector, such as a photo diode (silicon photo diode) or a photomultiplier tube, may be used.

Third Embodiment

In the second embodiment, one example of using a hemispherical lens, convex lenses, and a CCD camera (or a photo diode detector) is described as a hemispherical detection optical system. In the third embodiment, one example of using a rotational parabolic mirror 14 instead of the hemispherical lens 4 will be described with reference to FIG. 23. A hemispherical detection optical system according to the third embodiment comprises a rotational parabolic mirror 14, a convex lens system (convex lens) 13, and a CCD camera 6. The rotational parabolic mirror 14 has a shape cut (opening) along a plane perpendicular to the axis of rotation and passing through the focal point, and has a polished inner surface, and this mirror is disposed so that the cut plane (opening) passing through the focal point of this mirror is parallel to the edge of the quarter ellipsoidal mirror, and the focal point of this mirror coincides with that of the quarter ellipsoidal mirror.

Figure 23:
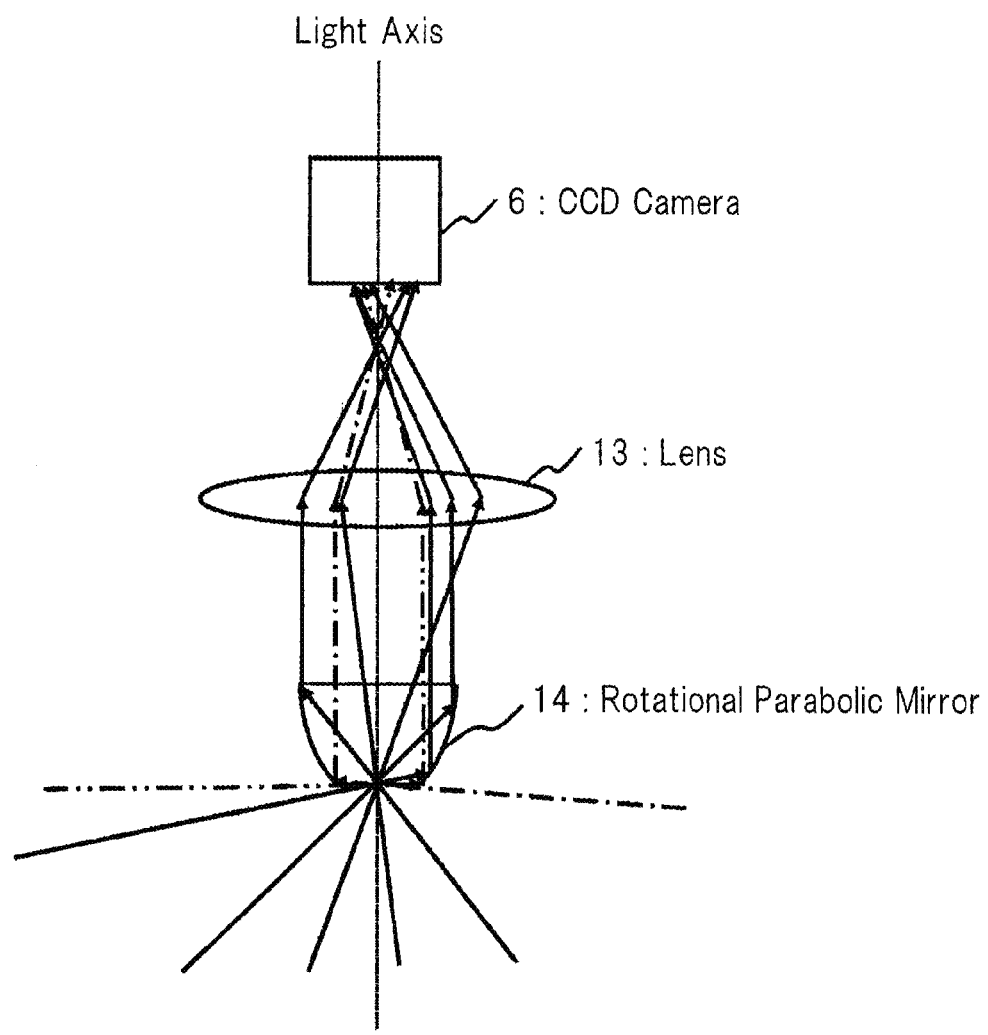
FIG. 23 is a view showing an optical characteristic measuring apparatus according to a third embodiment.

A dashed-dotted line and a dashed-two dotted line represent the same light rays as those of the second embodiment. In FIG. 23, a point at which five solid lines, the dashed-dotted line, and the dashed-two dotted line gather is a focal point F2 of the ellipsoidal mirror, and also coincides with the focal point of the rotational parabolic mirror. Light passed through a through hole provided at the focal point of the rotational parabolic mirror is reflected by the rotational parabolic mirror. The reflected Light proceeds parallel to an optical axis of the parabolic mirror, and is collected at a focal point of the convex lens 13. On the other hand, light that proceeds without being reflected by the parabolic surface is refracted by the convex lens 13, but is not collected at the focal point but gathers in the vicinity of the focal point. By disposing the CCD camera in a location where these light gather, it is possible to perform total light quantity measurement and light distribution measurement.

Fourth Embodiment

In the basic form using a rotational parabolic mirror shown in the third embodiment, as can be seen from FIG. 23, since the light collimated by the rotational parabolic mirror and diverging light from the focal point F2 may enter the same pixel of the CCD camera, strictly speaking, the measured light distribution is not precise. Therefore, the fourth embodiment has an improvement in measuring more precisely light distribution. An apparatus 1 according to the fourth embodiment is shown in FIG. 24, and an apparatus 2 in FIG. 25.

Figure 24:
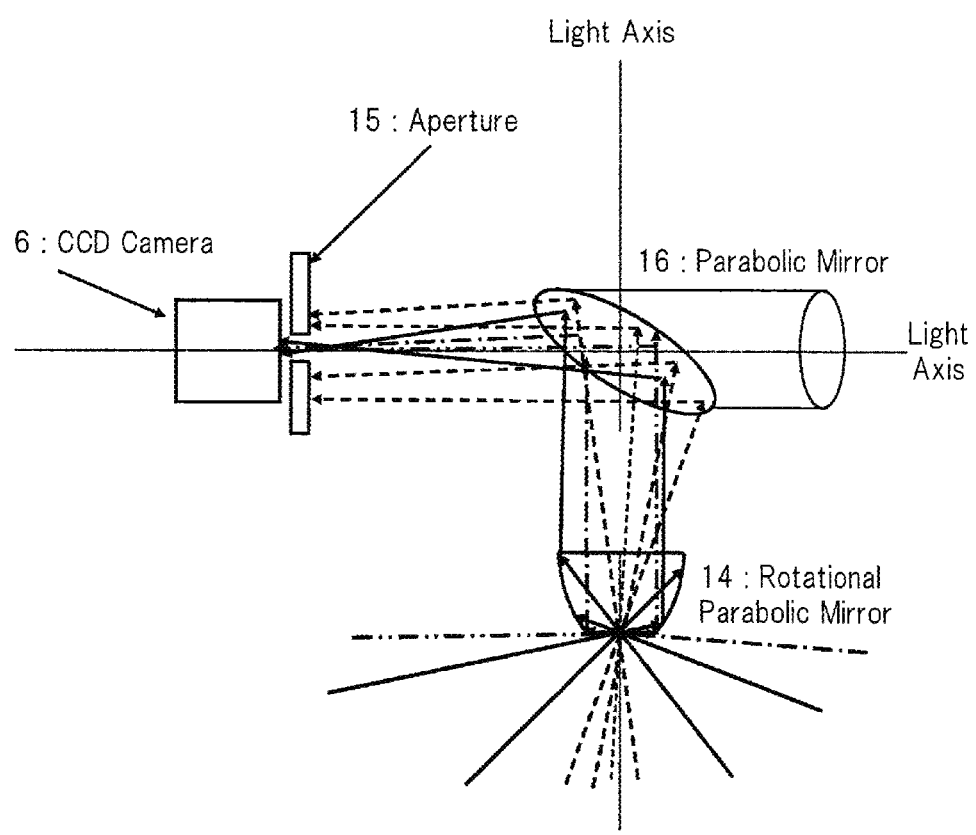
FIG. 24 is a view showing a fourth embodiment.

The apparatus 1, as shown in FIG. 24, is provided with a rotational parabolic mirror 14, a parabolic mirror 16, and a CCD camera 6 (or a detector such as a photo diode). In FIG. 24, a dashed-dotted line and a dashed-two dotted line represent light falling on the rotational parabolic mirror at an incident angle of almost 90 degrees, and these lines and solid lines become parallel after being reflected by the rotational parabolic mirror, and are reflected by the parabolic mirror above, and then collected to the detector. Light rays represented by broken lines are diverging light rays from the focal point of the ellipsoidal mirror, and these light rays are not reflected by the rotational parabolic mirror but reflected by the parabolic mirror above and blocked from reaching the detector by an aperture 15.

Figure 25:
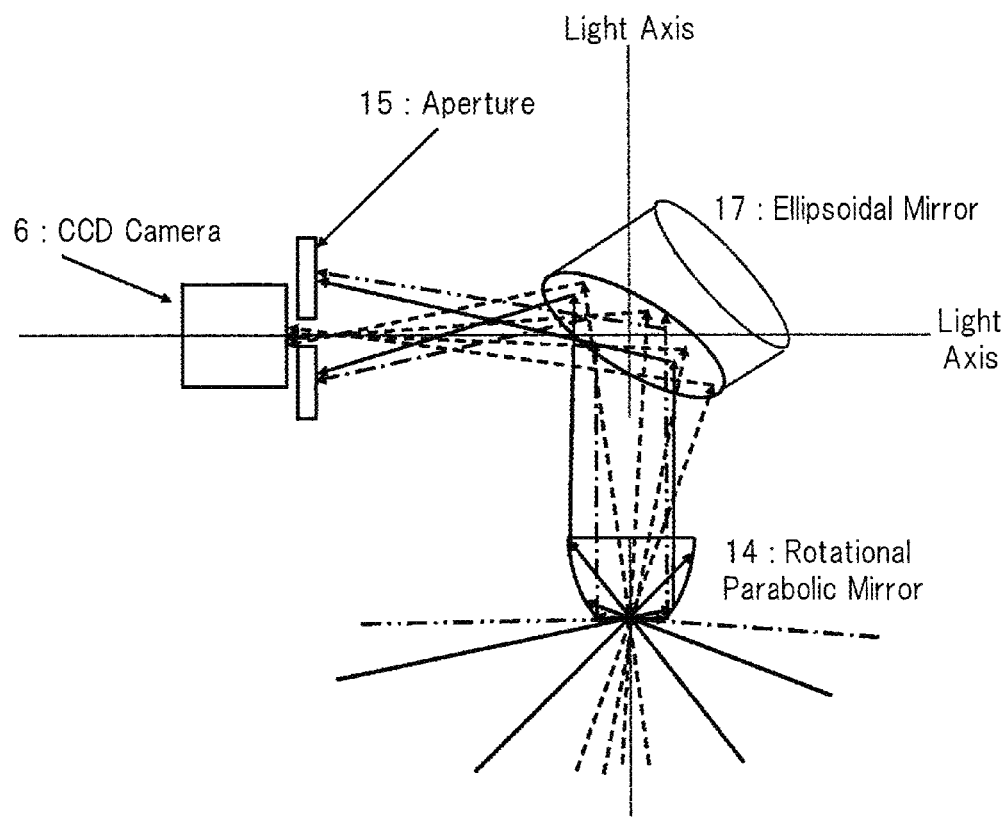
FIG. 25 is a view showing the fourth embodiment.
Figure 26:
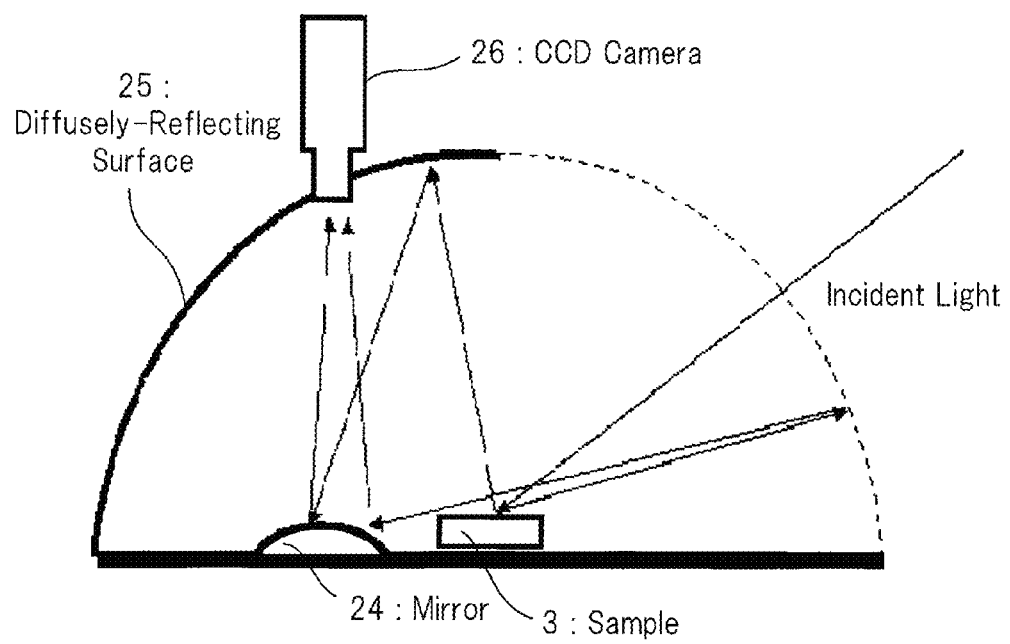
FIG. 26 is a view explaining a conventional technology.

The apparatus 2, as shown in FIG. 25, is provided with a rotational parabolic mirror 14, an ellipsoidal mirror 17, and a CCD camera 6 (or a detector such as a photo diode). In FIG. 25, a dashed-dotted line and a dashed-two dotted line represent light falling on the rotational parabolic mirror at an incident angle of almost 90 degrees, and these lines and solid lines become parallel after being reflected by the rotational parabolic mirror, and are reflected by the ellipsoidal mirror above, and blocked from reaching the detector by an aperture 15. Light rays represented by broken lines are diverging light rays from a focal point of the partial body of the ellipsoidal mirror, and these light rays are not reflected by the rotational parabolic mirror but reflected by the ellipsoidal mirror 17 above and reaches the detector.

Thus, as shown in FIG. 24, by arranging the parabolic mirror 16, the parallel rays from the rotational parabolic mirror can be collected to the detector (a CCD camera or a photo diode detector). On the other hand, light rays not reflected by the rotational parabolic mirror in FIG. 23 are a diverging light from a focal point of the partial body of the ellipsoidal mirror (also called "partial ellipsoidal mirror"), and can be collected to the detector by disposing the ellipsoidal mirror 17 instead of the parabolic mirror 16 (the apparatus 2, FIG. 25). In this embodiment, it is preferred that an aperture (aperture stop) 15 having a suitable diameter be disposed in front of the detector, if necessary. By disposing an aperture, diverging light can be eliminated when light is collected by the parabolic mirror 16, while parallel light rays can be eliminated when light is collected by the ellipsoidal mirror 17. By synthesizing these two images, light distribution can be measured.

The hemispherical detection optical system in the fourth embodiment is constituted by a combination of a rotational parabolic mirror, a reflective surface mirror (a term representing both a parabolic mirror and an ellipsoidal mirror), and a CCD camera, or constituted by a combination of a rotational parabolic mirror, a reflective surface mirror (a term representing both a parabolic mirror and an ellipsoidal mirror), and a photo diode detector. Since these hemispherical detection optical systems do not use an optical element utilizing refraction, such as a lens, these optical systems can also be used in any regions of ultraviolet, visible, and infrared wavelengths. Incidentally, the detector needs to be adapted to a measuring wavelength region.

In order to measure hemisphere total reflectance (transmittance), instead of the CCD camera 6, a photodetector, such as a photo diode (silicon photo diode) or a photomultiplier tube, may be used.

Examples in the above embodiments are described to facilitate understanding of the present invention, but the present invention is not limited to the embodiments.

While the present invention has been illustrated and described with respect to a particular embodiment thereof, it should be appreciated by those of ordinary skill in the art that various modifications to this invention may be made without departing from the spirit and scope of the present invention.

What is claimed is:

1. An optical characteristic measuring apparatus for measuring scattered light from an object, comprising:
    a double ellipsoidal optical system composed of a partial ellipsoidal mirror and a belt-shape ellipsoidal mirror, and a hemispherical detection optical system, wherein
    the partial ellipsoidal mirror has, at least, a structure cut along a plane passing through an axis of the double ellipsoidal optical system and a plane perpendicular to the axis and passing through a common focal point, and wherein
    the hemispherical detection optical system is disposed at a position of a focal point of the partial ellipsoidal mirror.

2. The optical characteristic measuring apparatus according to claim 1, wherein the hemispherical detection optical system is provided with a hemispherical lens which is disposed so that the center of the hemispherical lens coincides with the position of the focal point of the partial ellipsoidal mirror.

3. The optical characteristic measuring apparatus according to claim 2, wherein the hemispherical detection optical system is provided with a tapered optical fiber which is disposed so that a large-diameter side end face of the optical fiber coincides with the position of a focal point of the hemispherical lens.

4. The optical characteristic measuring apparatus according to claim 2, wherein the hemispherical detection optical system is provided with convex lenses and a photodetector, and light from the hemispherical lens is measured by the photodetector via the convex lenses.

5. The optical characteristic measuring apparatus according to claim 1, wherein the hemispherical detection optical system is provided with a rotational parabolic mirror which is disposed so that a focal point of the rotational parabolic mirror coincides with the position of the focal point of the partial ellipsoidal mirror.

6. The optical characteristic measuring apparatus according to claim 5, wherein the hemispherical detection optical system is provided with a reflective surface mirror and a photodetector, and light from the rotational parabolic mirror is measured by the photodetector via the reflective surface mirror.

7. The optical characteristic measuring apparatus according to claim 5, wherein the hemispherical detection optical system is provided with a convex lens and a photodetector, and light from the rotational parabolic mirror is measured by the photodetector via the convex lens.

8. The optical characteristic measuring apparatus according to claim 1, wherein the hemispherical detection optical system is provided with a CCD camera as a photodetector.

9. The optical characteristic measuring apparatus according to claim 1, wherein the partial ellipsoidal mirror is a quarter ellipsoidal mirror or an octantal ellipsoidal mirror.

\* \* \* \* \*